(12) United States Patent
Baughman et al.

(10) Patent No.: US 9,921,071 B2
(45) Date of Patent: *Mar. 20, 2018

(54) TRANSPORT OPTION SELECTION TO SERVE WELL-BEING OBJECTIVES

(71) Applicant: INTERNATIONAL BUSINESS MACHINES CORPORATION, Armonk, NY (US)

(72) Inventors: Aaron K. Baughman, Silver Spring, MD (US); Malolan Chetlur, Bangalore (IN); Christian Eggenberger, Wil (CH); Peter K. Malkin, Yorktown Heights, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/251,125

(22) Filed: Aug. 30, 2016

(65) Prior Publication Data
US 2016/0370198 A1 Dec. 22, 2016

Related U.S. Application Data

(63) Continuation of application No. 14/706,139, filed on May 7, 2015, now Pat. No. 9,464,906.

(51) Int. Cl.
*G01C 21/00* (2006.01)
*G01C 21/26* (2006.01)
(Continued)

(52) U.S. Cl.
CPC ........ *G01C 21/3453* (2013.01); *A61B 5/0205* (2013.01); *A61B 5/486* (2013.01);
(Continued)

(58) Field of Classification Search
CPC ...... G01C 21/00; G01C 21/34; G01C 21/206; G01C 21/3453; G01C 21/3484;
(Continued)

(56) References Cited

U.S. PATENT DOCUMENTS 6,349,261 B1 2/2002 Ohnishi et al.
9,464,906 B1 * 10/2016 Baughman ......... G01C 21/3469
(Continued)

OTHER PUBLICATIONS

Disclosed Anonymously, System and Methods for Managing Public Transport Vehicles and Providing Methods for Automated Connection Adjustment and Passenger Notification, IP.com Prior Art Database Technical Disclosure, May 2010.
(Continued)

*Primary Examiner* — Yonel Beaulieu
(74) *Attorney, Agent, or Firm* — Patrick J. Daugherty; Driggs, Hogg, Daugherty & Del Zoppo Co., LPA

(57) ABSTRACT

Aspects generate customized routes that select between human-powered and motorized transport option segments to maximize well-being objective in navigating a traveler to a destination. Amounts of human-powered transport options that a traveler is willing, able or recommended to perform via the traveler's own physical exertions in reaching a destination are determined as a function of well-being or cost objectives and performance limits. Recommended routes to the destination having human-powered and/or motorized transport option segments are generated that meet well-being objectives without exceeding amounts that the traveler is currently able to perform, and excluding segments that require efforts that do not meet the well-being objective or exceed the amounts that the traveler is currently able to perform.

20 Claims, 6 Drawing Sheets

(51) Int. Cl.
    *G01C 21/34*     (2006.01)
    *G01C 21/20*     (2006.01)
    *A61B 5/0205*     (2006.01)
    *A61B 5/00*     (2006.01)
    *G09B 5/02*     (2006.01)
    *G06F 19/00*     (2018.01)

(52) U.S. Cl.
    CPC .......... *A61B 5/4866* (2013.01); *G01C 21/206* (2013.01); *G01C 21/3469* (2013.01); *G01C 21/3484* (2013.01); *G09B 5/02* (2013.01); *G06F 19/345* (2013.01); *G06F 19/3481* (2013.01)

(58) Field of Classification Search
    CPC .... G09B 5/00; G09B 5/02; A61B 5/00; A61B 5/0205; A61B 5/486; A61B 5/4866
    See application file for complete search history.

(56) References Cited

U.S. PATENT DOCUMENTS

| | | |
|---|---|---|
| 2008/0077599 A1 | 3/2008 | Oni |
| 2012/0209512 A1 | 8/2012 | Kujirai et al. |
| 2013/0245943 A1 | 9/2013 | Hiestermann et al. |
| 2015/0324751 A1 | 11/2015 | Orenstein |

OTHER PUBLICATIONS

Rank LTD, Optimized Route Planning for Joint Travel, IP.com Prior Art Database Technical Disclosure, Aug. 2011.
J.O. Royset et al, Route Optimization for Multiple Searchers, Operations Research Department, Naval Postgraduate School, Sep. 2009.
Emil Protalinski, Microsoft Research built a smart elevator that uses AI to figure out what floor you're going to, http://thenextweb.com, Jan. 2014.
Jim Zarroli, Smart Elevators: A Faster Way Up and Down, Listen Morning Edition, http://www.npr.org, Jan. 2007.
U.S. Appl. No. 14/706,139, filed May 7, 2015.
Notice of Allowance (dated Jun. 21, 2016) for U.S. Appl. No. 14/706,139, filed May 7, 2015.

* cited by examiner

TRANSPORT OPTION SELECTION TO SERVE WELL-BEING OBJECTIVES

BACKGROUND

Human-powered transport, or active transport, are terms that refer to using human muscle power to generate power and perform work to overcome gravity, inertia or other properties or forces to travel or move (transport) one's self and/or another person or object from one location over distance to another location. Illustrative but not limiting or exhaustive examples of active, human-powered transport activities include crawling, shuffling, walking, running, bicycling, stair climbing or descending, swimming, water vessel rowing and water vessel paddling. Such activities may be loaded, wherein the traveler must exert enough energy to not only move themselves but also the mass of another person or object that they may be carrying or otherwise conveying.

A wide variety of motorized transport options are available to help a traveler achieve transport goals while exerting less energy or saving time relative to human-powered options. Energy savings are achieved using motor components that consume energy resources to generate power outputs, for example as deployed within motorcycles, automobiles, elevators, escalators and moving sidewalks, airplanes, trains, etc. Some motorized components also capture and convert environmental and renewal energy into motive power, for example, sailboats that harness the wind, canoes and barges conveyed downstream by flowing bodies of water, electric vehicles powered by solar (photovoltaic) cells, etc.

BRIEF SUMMARY

In one aspect of the present invention, a method automatically selects between human-powered and motorized transport options to produce a route to a destination that meets traveler well-being and cost objectives. The method includes determining a traveler's current location, a target destination location, and an amount of a human-powered transport option that the traveler is willing or recommended to perform via the traveler's own physical exertions in reaching the destination. A well-being objective of the traveler is determined that includes meeting an exercise goal, minimizing exposure to an environmental stressor, or limiting a physical demand placed on the traveler by exertion required to perform the human-powered transport option to a maximum amount. An amount that the traveler is currently able to perform of the indicated amount of the human-powered transport is determined as a function of a current status of the traveler and the well-being objective determining, and a recommended route generated to the destination from the current location that meets the well-being objective by including route segments of usage selected from available human-powered and motorized transport options. The selection of the route segments comprehends including segments of usage of the human-powered transport option that efforts that meet the well-being objective without exceeding amounts that the traveler is currently able to perform, and excluding segments that require efforts that do not meet the well-being objective or exceed the amounts that the traveler is currently able to perform.

In another aspect, a system has a hardware processor in circuit communication with a computer readable memory and a computer-readable storage medium having program instructions stored thereon. The processor executes the program instructions stored on the computer-readable storage medium via the computer readable memory and thereby determines a traveler's current location, a target destination location, and an amount of a human-powered transport option that the traveler is willing or recommended to perform via the traveler's own physical exertions in reaching the destination. A well-being objective of the traveler is determined that includes meeting an exercise goal, minimizing exposure to an environmental stressor, or limiting a physical demand placed on the traveler by exertion required to perform the human-powered transport option to a maximum amount. An amount that the traveler is currently able to perform of the indicated amount of the human-powered transport is determined as a function of a current status of the traveler and the well-being objective determining, and a recommended route generated to the destination from the current location that meets the well-being objective by including route segments of usage selected from available human-powered and motorized transport options. The selection of the route segments comprehends including segments of usage of the human-powered transport option that efforts that meet the well-being objective without exceeding amounts that the traveler is currently able to perform, and excluding segments that require efforts that do not meet the well-being objective or exceed the amounts that the traveler is currently able to perform.

In another aspect, a computer program product for automatically selecting between human-powered and motorized transport options to produce a route to a destination that meets traveler well-being and cost objectives has a computer-readable storage medium with computer readable program code embodied therewith. The computer readable program code includes instructions for execution which cause the processor to determine a traveler's current location, a target destination location, and an amount of a human-powered transport option that the traveler is willing or recommended to perform via the traveler's own physical exertions in reaching the destination. A well-being objective of the traveler is determined that includes meeting an exercise goal, minimizing exposure to an environmental stressor, or limiting a physical demand placed on the traveler by exertion required to perform the human-powered transport option to a maximum amount. An amount that the traveler is currently able to perform of the indicated amount of the human-powered transport is determined as a function of a current status of the traveler and the well-being objective determining, and a recommended route generated to the destination from the current location that meets the well-being objective by including route segments of usage selected from available human-powered and motorized transport options. The selection of the route segments comprehends including segments of usage of the human-powered transport option that efforts that meet the well-being objective without exceeding amounts that the traveler is currently able to perform, and excluding segments that require efforts that do not meet the well-being objective or exceed the amounts that the traveler is currently able to perform.

BRIEF DESCRIPTION OF THE DRAWINGS

These and other features of embodiments of the present invention will be more readily understood from the following detailed description of the various aspects of the invention taken in conjunction with the accompanying drawings in which.

DETAILED DESCRIPTION

Figure 1:
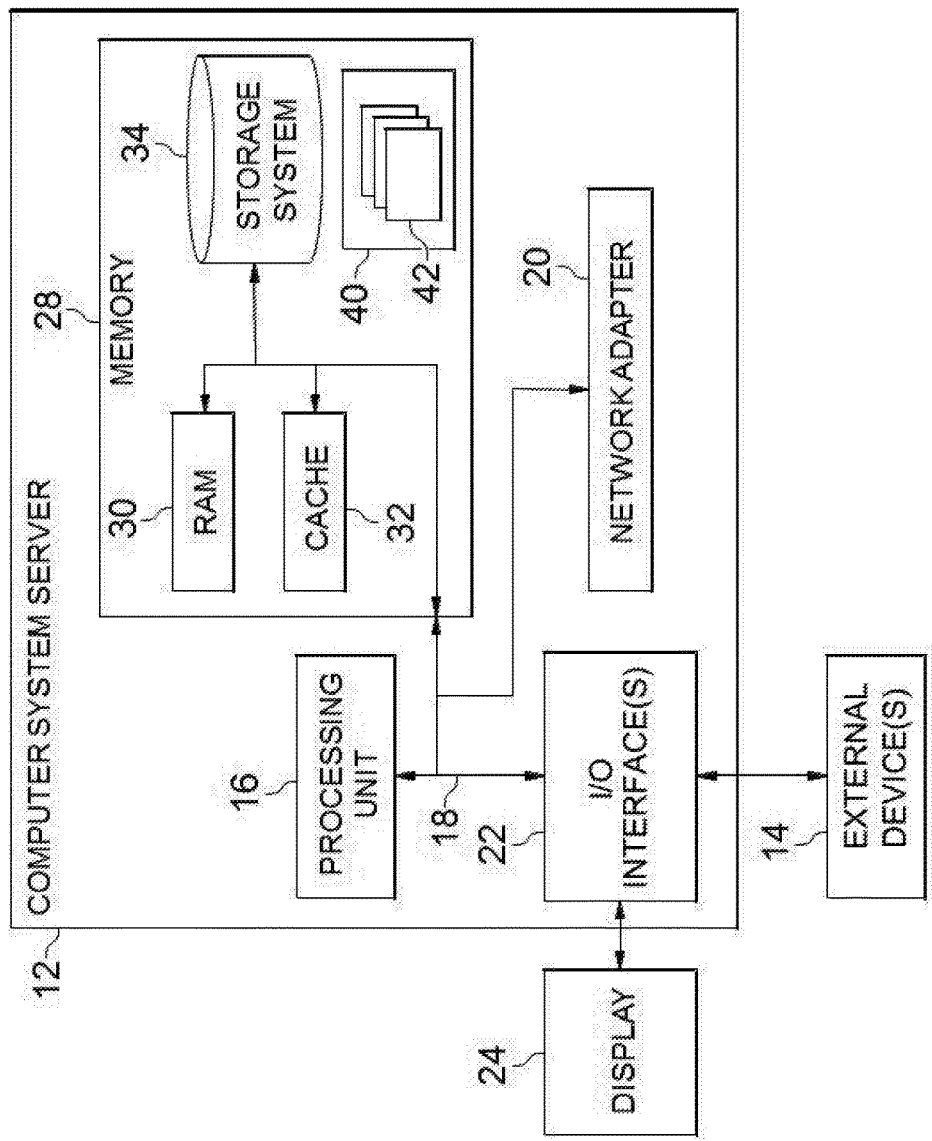
FIG. 1 depicts a cloud computing node according to an embodiment of the present invention.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Referring now to FIG. 1, a schematic of an example of a cloud computing node is shown. Cloud computing node 10 is only one example of a suitable cloud computing node and is not intended to suggest any limitation as to the scope of use or functionality of embodiments of the invention described herein. Regardless, cloud computing node 10 is capable of being implemented and/or performing any of the functionality set forth hereinabove.

In cloud computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 1, computer system/server 12 in cloud computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

Figure 2:
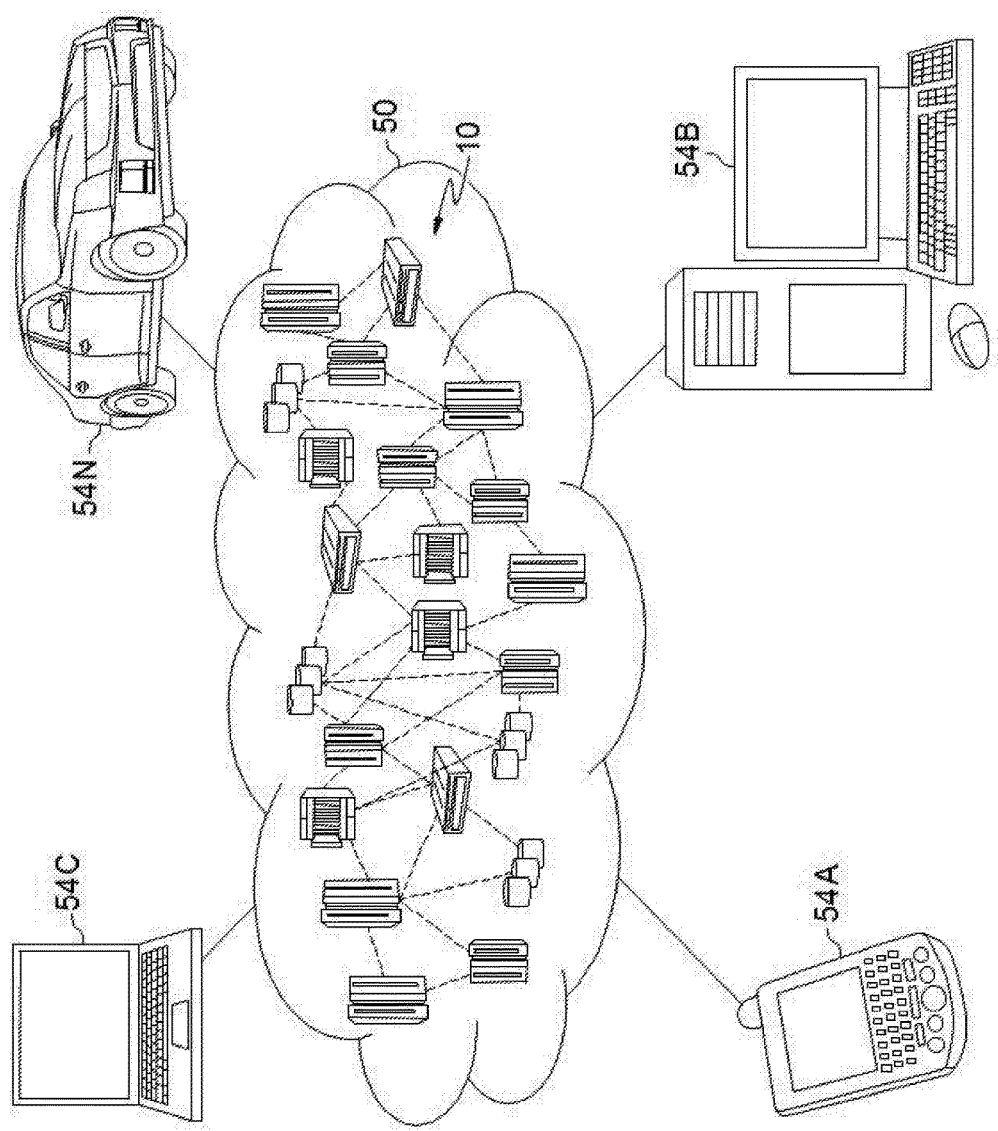
FIG. 2 depicts a cloud computing environment according to an embodiment of the present invention.

Referring now to FIG. 2, illustrative cloud computing environment 50 is depicted. As shown, cloud computing environment 50 comprises one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 2 are intended to be illustrative only and that computing nodes 10 and cloud computing environment 50 can communicate with any type of computerized device over any type of network and/or network addressable connection (e.g., using a web browser).

Figure 3:
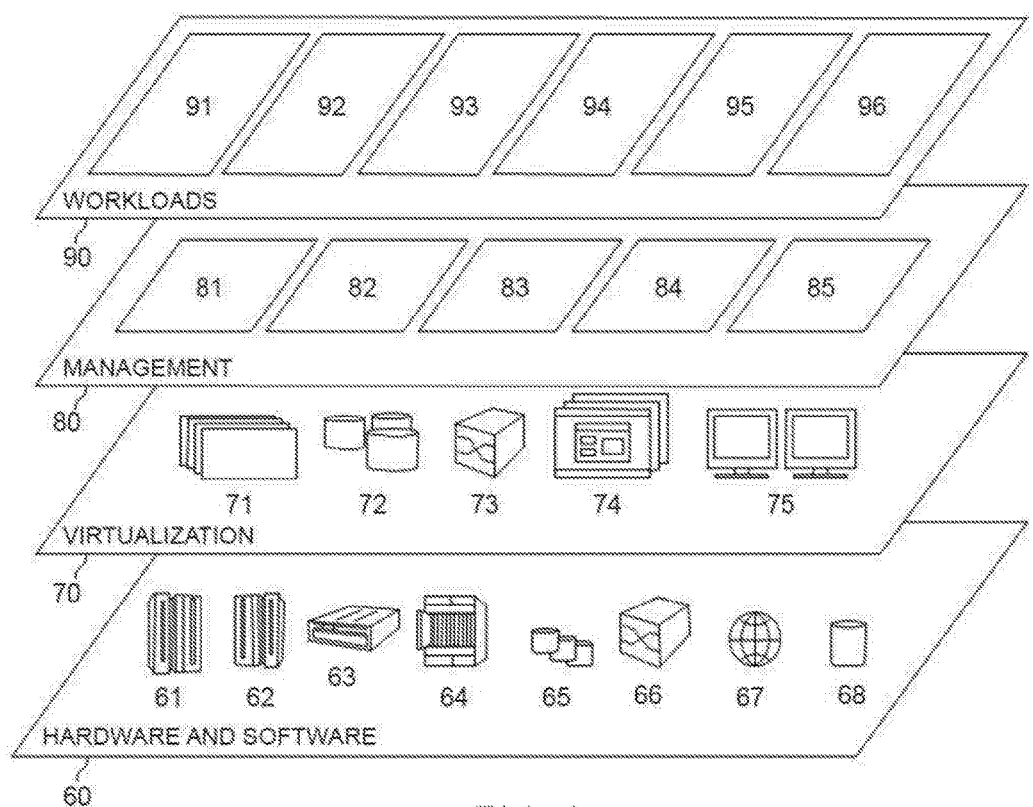
FIG. 3 depicts abstraction model layers according to an embodiment of the present invention.

Referring now to FIG. 3, a set of functional abstraction layers provided by cloud computing environment 50 (FIG. 2) is shown. It should be understood in advance that the components, layers, and functions shown in FIG. 3 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provides pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and automatically selecting between human-powered and motorized transport options to produce a route to a destination that meets traveler well-being and cost objectives 96, as described with particularity below.

In one aspect, a service provider may perform process steps of the invention on a subscription, advertising, and/or fee basis. That is, a service provider could offer to integrate computer readable program code into the computer system/server 12 to enable the computer system/server 12 to perform process steps of the invention. The service provider can create, maintain, and support, etc., a computer infrastructure, such as the computer system 12, bus 18, or parts thereof, to perform the process steps of the invention for one or more customers. In return, the service provider can receive payment from the customer(s) under a subscription and/or fee agreement and/or the service provider can receive payment from the sale of advertising content to one or more third parties. Services may include one or more of: (1) installing program code on a computing device, such as the computer device 12, from a tangible computer readable medium device 34; (2) adding one or more computing devices to the computer infrastructure 10; and (3) incorporating and/or modifying one or more existing systems 12 of the computer infrastructure 10 to enable the computer infrastructure 10 to perform process steps of the invention.

Motorized transport options provide increased speed and load capacity and reductions in required efforts by travelers relative to active, human-powered options. However, human-powered options may provide viable and desirable alternatives in serving a given destination. For example, their use may have lower costs, convey enjoyment and health benefits via the effects of physical exercise, reduce the usage of non-renewable resources, and enable travelers to avoid traffic congestion or crowds endemic to mass transit option. Accordingly, FIG. 4 (or "FIG. 4") illustrates a computer-implemented method or process of an aspect of the present invention for automatically selecting between human-powered and motorized transport options to produce a route to a destination that meets traveler well-being and cost objectives.

At 102 a processor (for example, a central processing unit (CPU)) executes code (for example, code installed on a storage device in communication with the processor) and thereby obtains or determines a traveler's current location and a location of a target destination that the traveler wishes to travel to (transport to) from the current location.

At 104 the processor determines, obtains or identifies an amount of a human-powered transport option that the traveler is currently willing or recommended to perform or execute via the traveler's own physical exertions in reaching the destination. The amount of the human-powered transport option may be distance travelled thereon (step count, distance covered, elevation gained or lost, pedal rotations, etc.); a time of travel; a total exertion that the traveler is willing to expend in executing or performing the human-powered transport option (for example, calories burned, maximum heart rate, etc.); effort as a function of time (for example, to achieve for a target time period a heart rate that meets a specified rate or heart rate zone range of rates, a calorie burn rate, a pedal cadence, a power output rate, etc.); and still other quantified amounts of execution of a human-powered transport option will be apparent to one skilled in the art.

At 106 the processor determines, obtains or identifies one or more routing well-being objectives. The routing objectives may include a variety of goals, such as to minimize travel time or number of stops of a motorized transport option (for example, elevator, bus, train, cab, etc.) required to transport the traveler and/or other persons, or desired maximum amounts of time available to reach the destination. Cost objectives may also be considered, for example to minimize mass transportation fares or keep total costs of resources expended on motorized transport route options. The cost objective may be energy related, for example, a goal to minimize overall energy consumed by motorized transport route options, or to favor the use of renewable over non-renewable energy.

The well-being objectives serve or maximize the well-being of the traveler, for example an exercise goal or target workout achievement (goal for number of steps per day, distance to walk, time to raise heart rate to a value within a target zone, etc.), in some examples as a function of a current affective or somatic state of the traveler, for example as indicated or measured by traveler Heart Rate Variability (HRV) data.

Serving a well-being objective of the traveler may also result in recommendations to avoid exposure to inclement weather or other environmental stressors. For example, bad weather conditions (e.g. heavy rain, strong wind, etc.) may be recognized as an influencing factors or inputs, wherein outdoors routing option portions (walking, biking, stair climbing, etc.) may be weighted to discourage or prevent selection over sheltered motorized transport options for said portions during the duration of rain or sub-zero temperatures, etc. Well-being objectives may also maximize physical demands or stresses placed on the traveler by exertions required by human-powered transport options (for example, cap total time or steps of exertion for a set time period), or those associated with motorized transport options (for example, minimize crowding, exposures to contagious fellow mass transit passengers, avoid rush hour, etc.).

At 108 the processor optionally determines one or more routing performance limits, requirements, maximums or thresholds that routing solutions (or human-powered or motorized segments thereof) must meet. For example, the route may be required to generate a projected arrival time at the destination by or before an appointment time, or not exceed a specified total travel time, fare cost, energy consumption amount, number of stops, etc. Performance limits may also be related to physical demands placed on the traveler in reaching the destination or in performing an amount of a human-powered transport option, such as specifying a maximum heart rate that the traveler is allowed to achieve for the traveler's age or BMI, or in view of traveler Heart Rate Variability (HRV) data that indicates a revised target rate that is above or below that indicated by age, etc.

At 110 the process determines an amount of the indicated amount of the human-powered transport option that the traveler is currently able to perform in reaching the destination as a function of a current status of the traveler and the well-being objective. The determination at 110 may consider performance limits. For example, a current physical status data of the traveler may be determined, obtained or identified that is relevant to mobility or physical exertion capacities of the user in executing any selected human-powered transport option. Illustrative but not limiting or exhaustive examples include real-time health monitor data and stored (historic) values of heart and/or respiration rates, current moving speed, body temperature, body mass index (BMI), weight, blood sugar, cholesterol, and other blood test profile data; current medications; and diagnosed, indicated or reported illnesses injuries or physical condition.

In some aspects, mobility capacity is determined from current health sensor or movement data by comparison to historic or expected health monitor data values for the traveler. For example, a slower-than-normal pace of movement or gate, with or without health sensor data indicating the traveler is exerting higher than normal exertions levels, may indicate that the traveler is carrying a package, small child or other load and therefore less likely to be able to generate the energy required for human-powered transport options in the amounts indicated at 104. Current gait data may indicate that the traveler is on crutches, has an injured foot or leg, or is fatigued or physically impaired, sometimes relative to the traveler's normal gait. Thus a performance limit may be applied at 110 that reduces willing amounts of exertion determined at 104 to lower "able" amounts, in recognition of the traveler's observed status that caps or lowers the amount of effort the traveler has indicated that they are currently willing or able to perform.

In some aspects, the "ability" amount of the traveler assessed at 110, or the "willingness" amount assessed at 104, are attributes of the transport options that the traveler is amenable to select or reject, such as whether to share a given transport option with other identified fellow travelers. Thus, social network relationship status relevant to other potential passengers on route transport options may be acquired at 104 or 110. For example, in order that a shared transport experience may be more pleasant or productive, LinkedIn® Wikipedia™, Facebook®, Twitter® or other social network feeds and data of the traveler may be analyzed to identify friends, colleagues and other people indicated as desirable for selection as fellow motorized transport option passengers; or to identify people indicated as undesirable and to be avoided for selection as fellow motorized transport option passengers, such as former colleagues associated with an employment termination event, or an "un-friended" person, etc. (LINKEDIN is a trademark of the Linkedin Corporation in the United States or other countries; WIKIPEDIA is a trademark of the Wikimedia Foundation in the United States or other countries; FACEBOOK is a trademark of Facebook, Inc. in the United States or other countries; TWITTER is a trademark of Twitter, Inc. in the United States or other countries.)

Serving the well-being objective of the traveler at 110 may also recognize a desirability or requirement to avoid exposure to inclement weather or other environmental health stressors that may cause or aggregate illness. For example, bad weather conditions (e.g. heavy rain, strong wind, sub-zero temperatures, etc.), smog or ozone alert conditions, etc., may be recognized as influencing factors or inputs at 110, so that outdoors routing option portions (walking, biking, stair climbing, etc.) may be weighted to discourage or prevent selection over alternative sheltered motorized transport options for said portions during a duration (or forecast occurrence) of the inclement weather or environmental stressor conditions. In some aspects, this weighting may be dependent on current health data, to change the weighting to discourage available human-powered option portions while the traveler data indicates that the traveler is un-well. The weighting may also vary the amount of the available human-powered route portions used, for example shortening the length of a human powered route option by a percentage value in response to recognizing (via HRV or other health data) that the traveler is not at optimal health or recovery levels.

At 112 the process generates a recommended route to the destination from the current location that meets the well-being objective by including one or more route segments of usage selected from available human-powered and motorized transport options. The recommended route segment(s) are selected to enable the route to meet the well-being or cost objective(s), and in some examples to comply with any performance limit(s), wherein the selection includes or excludes ones of the available human-powered transport options as a function of comparing the exertions required to the amounts that the user is currently willing, able or recommended to perform or execute via the user's own physical exertions. Thus, the route segment selection may include a first of the human-powered transport options that requires a first amount of effort that meets the well-being objective and does not exceed the amount of the human-powered transport option that the traveler is currently able to perform. Or, it may exclude a second of the human-powered transport options that requires an amount of effort that does not meet the well-being objective or exceeds the amount of the human-powered transport option that the traveler is currently able to perform.

Selection or creation of a recommended route at 112 in response to the inclement weather or environmental stressor objectives input at 110 and discussed above may result in selection of sheltered motorized transport options in the alternative to available human-powered possibilities for route portions that would otherwise have been selected, for example to meet traveler objectives. Thus, a first route may be generated for execution over a time period having (or predicted to have) good weather or environmental conditions (for example, pleasant temperatures, safe smog and ozone levels, no rain) that directs the traveler to disembark a bus (motorized transport option) three stations prior to the station closest to his/her destination, in order to use a human-powered option (walk, bike, climb stairs, etc.) for a remainder of the route to the destination, thereby serving an exercise goal or cost or carbon energy usage minimization objective in reaching the destination. However, if the same time period is instead experiencing (or predicted to experience) poor weather (heavy rain, etc.) or poor environmental conditions (smog or ozone alert levels, etc.), then instead a different, second first route may be generated that directs the traveler to remain on the bus until disembarking at the station closest to his/her destination. Thus, the aspect may minimize exposure to poor weather or environmental health stressors, serving an objective to avoid aggravating a current ill condition of the traveler or otherwise to keep the traveler healthy. In this example, the traveler is spared being instructed to leave the bus earlier and walk in the rain (via the first route) in response to neglecting to manually change exercise willingness or objective inputs in view of the poor weather: the present aspect will automatically do this for the traveler.

At 114 the recommended route is presented to the traveler. In some aspects, the route may be dynamically revised while the traveler progresses to the destination, thus periodically or in response to another prompt determining whether or not the traveler has arrived at 116, and re-assessing the current status and ability of the traveler relative to the well-being objective at 110 and re-generating a recommended route according to 112, until the user arrives at 116 (wherein the process ends at 118).

Figure 5:
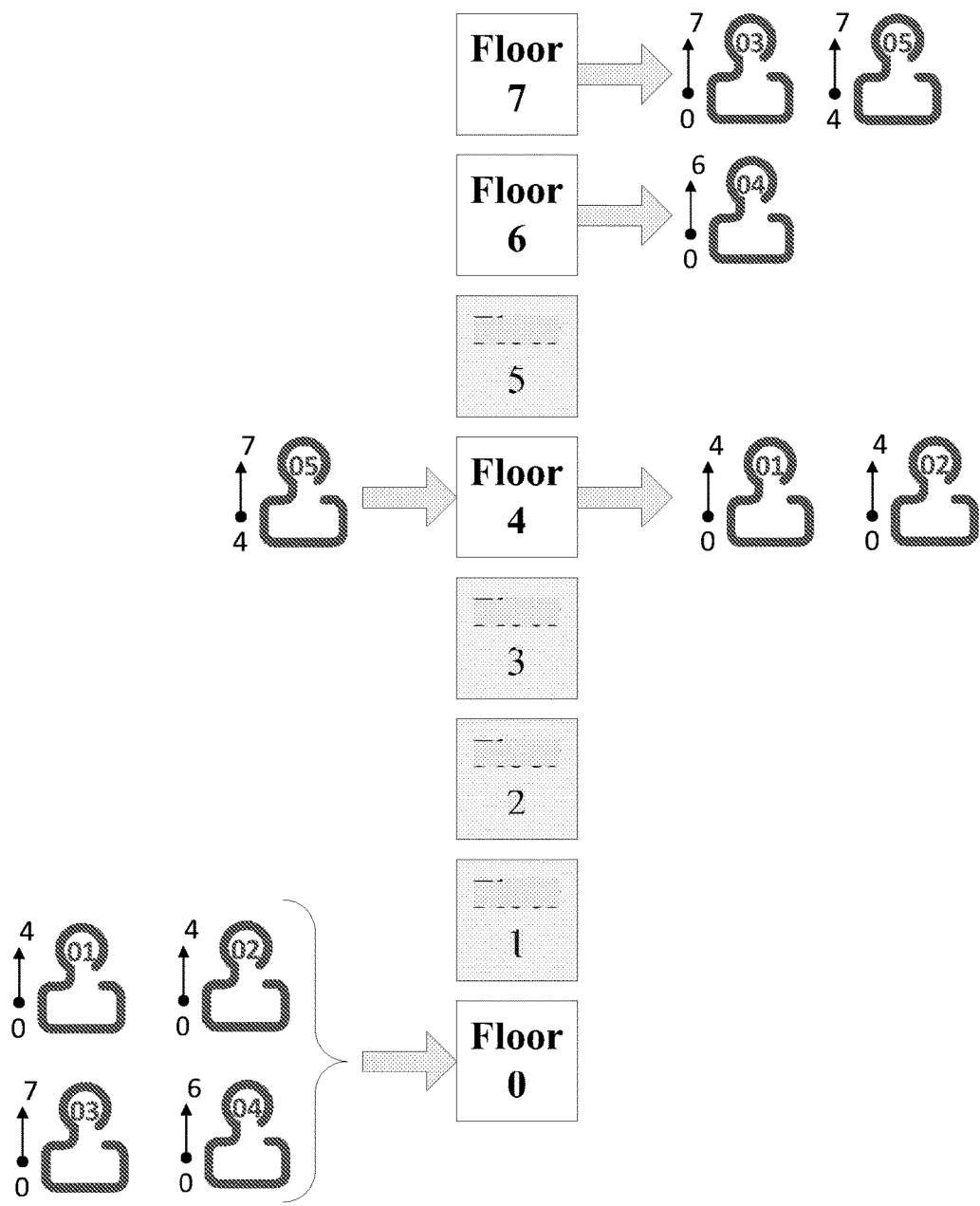
FIG. 5 is a graphical illustration of prior art routing of travelers to different floor destinations in a multi-story building.

FIG. 5 illustrate a conventional elevator usage wherein five different travelers 01, 02, 03, 04 and 05 use the same elevator to arrive directly at their respective desired destinations. The starting and desired destination floors for each traveler are indicated by the arrow icons located on the left side of each traveler icon, with the lower number representing the starting position and the upper number the destination (for example, the starting position for traveler 01 is the ground floor, floor 0, and the destination is floor 4). Thus, travelers 01, 02, 03 and 04 enter the elevator cage together at the ground floor ("Floor 0") and select floors 4, 4, 7 and 6, respectively, on the elevator control panel. At floor 4 travelers 01 and 02 exit, and traveler 05 enters and requests floor 7. The car continues upward, stopping at floor 6 to let out traveler 04, and then at floor 7 to let out travelers 05 and 03.

The total trip represented in FIG. 5 requires energy to generate three upward accelerations and corresponding decelerations by the elevator as loaded. The trip also consumes energy to do work in overcoming gravitation forces and moving the weight of the four travelers 01, 02, 03 and 04 upward from floor 0 to floor 4, the weight of the three travelers 03, 04 and 05 upward from floor 4 to floor 6, and the weight of the remaining two travelers 03 and 05 upward from floor 6 to floor 7. The elevator has done all of the work in moving the passengers directly to their desired floors, and no stairs are used by any of the passengers, resulting in no exercise benefits.

Passengers may opt to take stairs to travel between floors in a building instead of using an elevator. Generally, the willingness of a traveler to take a stairway flight to travel between floors is inversely proportional with increasing the number of floors to climb up or down. This may be especially true for buildings with many floors.

Figure 4:
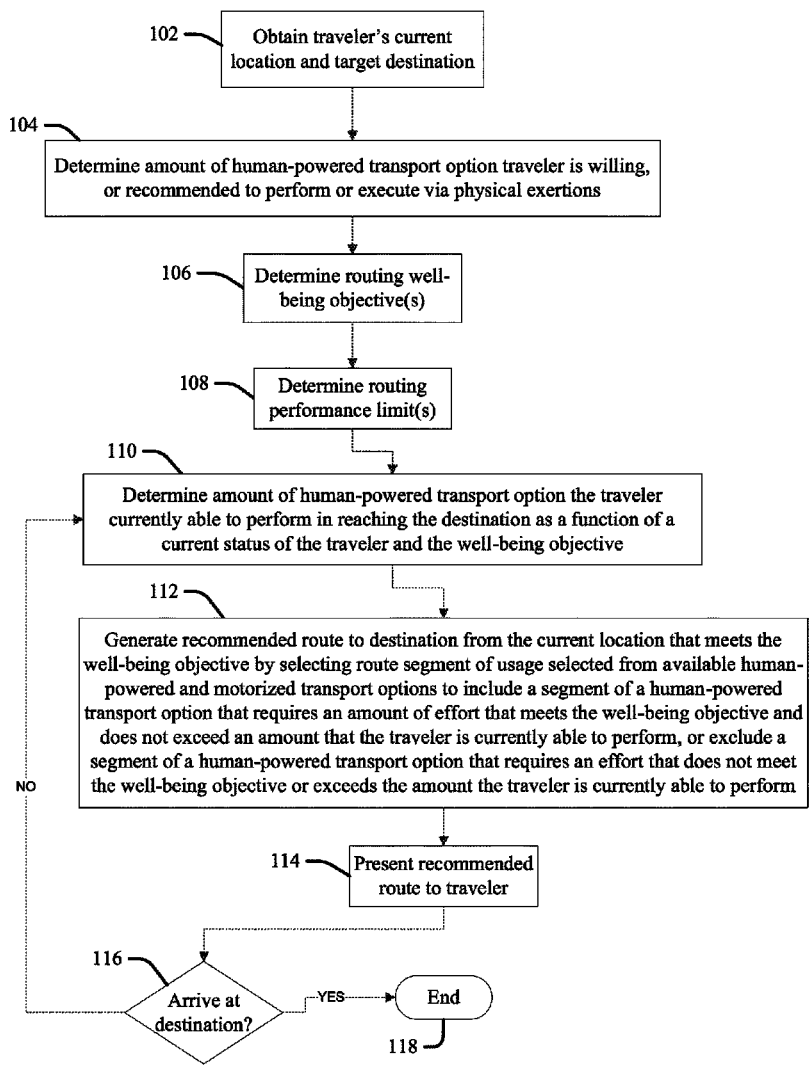
FIG. 4 is a flow chart illustration of a method or process for automatically selecting between human-powered and motorized transport options to produce a route to a destination that meets traveler well-being and cost objectives according to an embodiment of the present invention.
Figure 6:
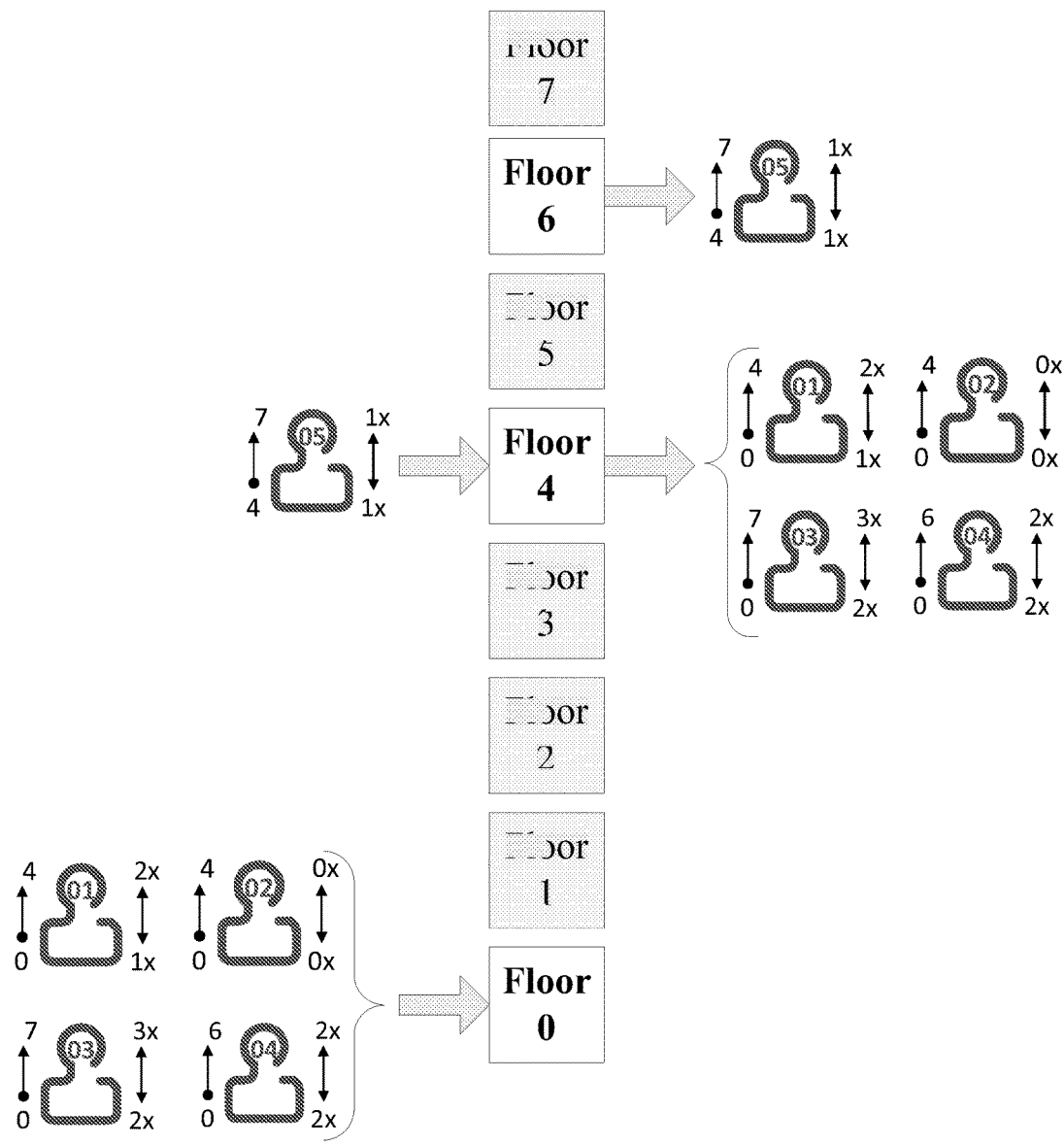
FIG. 6 is a graphical illustration of routing of travelers to different floor destinations in a multi-story building according to an embodiment of the present invention.

FIG. 6 illustrates an example of automatically generating and executing alternative routing for the same travelers 01, 02, 03, 04 and 05 via the process of FIG. 4, wherein data acquired with respect to each traveler (at 104, FIG. 4) indicates the numbers of flights of steps that they are willing and able to ascend or descend in routing their destination. More particularly, the top numbers of the double-headed arrows located on the right side of each traveler icon indicate the maximum flights that they can ascend, while the bottom numbers of the double-headed arrows indicate the maximum flights that they can descend (for example, traveler 01 is willing and able to ascend two flights and to descend one flight).

In one example, data used to determine the willing and able ranges is transmitted from smart phone or other personal digital assistant (PDA) mobile devices carried by each traveler to the optimizing system via BlueTooth™ or other wireless communications. (BLUETOOTH is a trademark of Bluetooth SIG, Inc., in the United States or other countries.)

The present example calculates optimum route planning solutions for each of the different travelers by considering their indicated willingness/capability to climb up or down stairs and using this information to generate custom destination routing that includes human-powered (stairway usage) portions or legs where appropriate. The resultant routing reduces the total number of stops needed to satisfy the needs of each traveler in reaching their destinations, thereby saving electrical energy resources for conveying loads and accelerating and decelerating the cabs, reducing travel time on the elevator, while identifying and creating opportunities for the travelers to exercise or otherwise engage in physical activity at a level corresponding with their indicated willingness, increasing the overall happiness and well-being of the travelers.

Thus, in FIG. 6 the travelers 01, 02, 03 and 04 are each directed to disembark at floor 4 as a function of determinations (at 104 and 110) of the human-powered options amounts that each is willing and able to execute. More particularly, it is determined that traveler 02 cannot (or should not) either ascend or descent any steps (perhaps due to an injury, current biometric readings of concern, carrying a heavy object, etc.), and is accordingly delivered directly to his/her desired floor.

Although traveler 01 is willing and able to ascend two flights or descend one flight to reach the final destination, no other stops are projected to serve the needs of the other travelers that include a stop two flights below this stop or one flight above, so traveler 01 is taken directly to and instructed to debark at the requested destination.

Traveler 03 is willing and able to ascend three flights or descend two flights, and gets his/her wish: instructed to debark at floor 4 and to ascend three flights to reach his/her floor 7 destination, getting the maximum desired physical activity. Traveler 04 is willing and able to ascend or descend two flights, and is therefore instructed to debark at floor 4 and take two flights up to reach destination floor 6. Note that the elevator is actually going on to a stop at this destination floor 6, and a conventional elevator would merely take traveler 04 on to floor 6. But the present example instead prompts traveler 04 to debark and get the indicated, appropriate exercise and instead take the stairs to reach floor 6: this results in increasing the well-being of traveler 04, while also saving the energy otherwise expended in carrying him/her up to floor 6 via the elevator.

Remaining traveler 05 enters the elevator at floor 4 and is now conveyed upward to floor 6, rather than all the way to his/her final destination floor 7 as in FIG. 5. Thus, traveler 05 gets the well-being benefit of ascending a flight of the stairs, meeting the willing and able amount determined for the traveler while enabling the traveler to reach floor 7 without having to send the elevator up to that floor: this results in increasing the well-being of traveler 05, while also saving the energy otherwise expended in carrying him/her up to floor 7 via the elevator.

Thus, routes are customized for each traveler, wherein combinations of human-powered (stair flights) and motorized (elevator ride) transport options are combined to produce destination routes that meet traveler well-being objectives, here by selecting or creating stair flight portions for passengers that indicate a willingness or desire to take the stairs when possible, practical or logical. Energy is harvested from the travelers themselves in order to augment the lower expenditures of energy used by the elevator to help get the travelers to their destinations.

The routes of FIG. 6 may also be created to meet cost objectives by reducing total energy used by the elevator relative to conventional routing of FIG. 5. Now only two upward accelerations and corresponding decelerations are required by the elevator, along with a lesser consumption of energy required to do work in overcoming gravitation forces to move total passenger loads upward. Four of the travelers (01, 02, 03, 04) now disembark at floor 4, and only one remaining traveler (05) is conveyed farther upward to floor 6 (rather than the weight of the three travelers 03, 04 and 05 carried in FIG. 5). Further, the car now stops at floor 6, no energy expended to move the car onward and upward to floor 7. Rather than move travelers 03, 04 and 05 directly to their desired floors, each of these travelers now execute part of their routes by human-powered flight of stairs portions, wherein the amount traveled within each of the human-powered portion is selected to be within the amounts that each indicates they are willing to execute. Less energy is used by the elevator, and travelers 03, 04 and 05 each experience an exercise benefit by taking the stairs.

A wide variety of cost objectives may be considered at 106, performance limits at 108, and abilities or attributes of the travelers at 110, to generate custom routing at 112. Aspects may consider differences in energy profiles between available elevators to select between elevators for portions for the customized routes. In skyscrapers and other large buildings different elevators may serve different ranges of floors (for example, one for floors 1-10, another for floors 11-20, etc.), or have different travel speeds or numbers of floors served (for example, a fast-ride or express elevator which stops only at a few floors, compared to a general service elevator that stops at more floors. Different elevators serving the same subsets of floor may also have different energy usage profiles, for example, an elevator which stops at each floor consumes more energy by constantly accelerating and decelerating the passenger cage.

The energy utilization pattern of a fast-track elevator may be different than that of a slower, many stop elevator. The fast-track elevator might also have a higher workload in the morning, at lunch time (due to serving restaurant options on a different floor from workers), and in the evening when a large number of people have to be distributed over a longer distance to enable egress from the building. A slower elevator might have a higher workload during other periods, for example serving people who have to change the floors within their department or company during working (non-lunch) hours.

Thus, the differing energy profiles described above may also be used to select between elevators available for use in a portion of a route: choosing a first over a second to save energy where energy maximization is a cost objective, or a faster third over the first to save time where time minimization is a cost objective.

Optimal loading and unloading strategy for each elevator cage may be based on current elevator cage position, acceleration speed, the passengers' current locations, estimated time requirements for the passengers to reach an elevator entrance at a certain floor or enter an elevator (for example, estimating longer times for traveler's traveling with crutches or carrying children or other loads). The social media data described above may be used to choose elevators loaded with "friend" passengers, and avoid those carrying people that the traveler would wish to avoid.

Performance limits considered at 108 for use in the route calculations include maximal velocity of the elevator, maximum weight load capacity of the elevator cage, available time of each passenger to reach their desired floors (for example, a passenger rushing to a scheduled or urgently requested meeting versus another passenger with no immediate schedule requirements), and floors each passenger has the permission to enter.

Data indicative of passenger ability or availability for an elevator ride or stairway usage route segment gathered or determined at 110 includes weight of the traveler relative to current loading and maximums for the elevator cab. Current biometric information of each traveler (BMI relative to overweight/underweight standards, current heart rate relative to expected heart rate for time of day, activity (walking, standing, etc.)) may be used to determine or confirm that the ability of the traveler (at 110) matches the willingness to climb or descend stairs indicated at 104.

Generating routes at 112 as a function of the cost objectives or performance limits may include prioritizing or balancing between different costs and limits. For example, traveler well-being may be prioritized or service first, over energy savings objectives. Further, maximizing the well-being or cost objective of travelers may be prioritized, with some objectives or travelers prioritized over others. For example, the selection of the routing illustrated in FIG. 6 takes traveler 01 directly to floor 4 even though it is determined that he or she is willing and able to ascend or descend flights of stairs as part of his or her route. This may be a function of determining that the other travelers 02-05 have higher priority needs to use the stairs (for example, they are further behind in their respective exercise goals for the day, and traveler 01 has met his or her goal), and/or that a cost objective requires routings to avoid additional stops when possible to reduce energy costs.

Thus, while adding a stop at floor 2 or at floor 5 and instructing traveler 01 to debark and use stairs to reach floor 4 accordingly to his or her "willing and able" status would generally serve a first "well-being" cost objective of traveler 01, such an additional stop may be unnecessary with respect to meeting a second, higher priority daily exercise goal objective or limit applicable to traveler 01, and also contrary to a third cost objective or performance limit that minimizes the number of stops used in routing travelers. Thus, an additional stop otherwise indicated by application of the first objective is ruled out by application of the second and third objectives, resulting in the routing illustrated in FIG. 6.

Thus, cost objective or performance limits may include minimizing the energy consumption of the elevator via reducing energy usage created by unnecessary or low priority stops, and minimizing a number stops based on expected utilization of the elevator to conform to an expected usage pattern, which may be time-dependent (weekday, daytime, lunchtime weekend, etc.). Maximizing enjoyment and the affective state of passengers may be served by selecting stops to create co-occupancies of traveler's friends, and/or to prevent entry of others that may trigger feelings of antipathy among passengers (for example, having the elevator move past such a person and route another elevator to serve that person. Objectives and limits may result in dropping stops to reduce overall travel time or minimize time taken to reach desired floors, in response to identified traveler profiles or attributes that indicate extended loading times may be required, for example to enable slower, less rushed ingress and egress opportunities for customers, children, passenger with disabilities, passengers without profile data, passengers with baggage items, etc.

The terminology used herein is for describing particular aspects only and is not intended to be limiting of the invention. As used herein, the singular forms "a", "an" and "the" are intended to include the plural forms as well, unless the context clearly indicates otherwise. It will be further understood that the terms "include" and "including" when used in this specification specify the presence of stated features, integers, steps, operations, elements, and/or components, but do not preclude the presence or addition of one or more other features, integers, steps, operations, elements, components, and/or groups thereof. Certain examples and elements described in the present specification, including in the claims and as illustrated in the figures, may be distinguished or otherwise identified from others by unique adjectives (e.g. a "first" element distinguished from another "second" or "third" of a plurality of elements, a "primary" distinguished from a "secondary" one or "another" item, etc.) Such identifying adjectives are generally used to reduce confusion or uncertainty, and are not to be construed to limit the claims to any specific illustrated element or embodiment, or to imply any precedence, ordering or ranking of any claim elements, limitations or process steps.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer-implemented method for automatically selecting between human-powered and motorized transport options to meet a well-being objective, the method comprising executing on a processor the steps of:
   determining a well-being objective of a traveler that is selected from the group consisting of meeting an exercise goal, minimizing exposure to an environmental stressor, and limiting a physical demand placed on the traveler by exertion required to perform a human-powered transport option to a maximum amount, and wherein the environmental stressor is selected from the group consisting of a poor weather condition, a poor smog level condition and a poor ozone level condition;
   determining an amount of the human-powered transport option for the traveler to perform to meet requirements of the well-being objective; and
   generating a recommended route to a destination from a current location of the traveler that meets the well-being objective by selecting between route segment portions of usage of the human-powered option and of a motorized transport option, the generated route including selections from the group consisting of:
   including a first segment of usage of the human-powered transport option in response to said included first segment requiring an amount of effort that meets the well-being objective and does not exceed an amount of the human-powered transport option that the traveler is currently able to perform; and
   excluding a second segment of usage of the human-powered transport option in response to said excluded second segment requiring an amount of effort that does not meet the well-being objective or that exceeds the amount of the human-powered transport option that the traveler is currently able to perform.

2. The method of claim 1, wherein the amount of the human-powered transport option that the traveler is currently able to perform is selected from the group consisting of:
   a distance travelled;
   a step count;
   a number of flights of stairs;
   an amount of elevation gained or lost;
   a number or rate of pedal rotations;
   an elapsed time of travel;
   a number or rate of calories burned;
   a specified value or range of values of heart rate of the traveler; and
   a power output value.

3. The method of claim 1, wherein the step of generating the recommended route to the destination is further a function of meeting a cost objective by minimizing an cost item selected from the group consisting of:
   a travel time;
   a number of stops of a motorized transport option;
   a monetary cost to the traveler for use of a motorized transport option;
   an amount of energy consumed by a motorized transport option; and
   an amount of use of non-renewable energy by a motorized transport option relative to an available use of a renewable energy.

4. The method of claim 1, wherein the well-being objective comprises a goal to maximize a well-being of the traveler by including a use of the human-powered transport option for a portion of the generated route in an amount that meets the exercise goal of the traveler.

5. The method of claim 1, further comprising:
   determining the amount of the human-powered transport option that the traveler is currently able to perform by:
   comparing real-time health monitor data indicative of the current status of the traveler to expected health monitor data values for the traveler; and
   in response to determining that the real-time health monitor data of the traveler is lower than the expected health monitor data values, reducing an amount of the human-powered transport option that the traveler is currently able to perform.

6. The method of claim 1, further comprising:
   analyzing social network data of the traveler to identify a friend of the traveler that is desirable for selection as a fellow motorized transport option passenger, or to identify another acquaintance of the traveler that is undesirable for selection as a fellow motorized transport option passenger; and
   generating the recommended route to meet the well-being objective by including a step selected from the group consisting of selecting a route segment of usage of the motorized transport option that includes the friend as a passenger, and omitting a route segment of usage of the motorized transport option that includes the another acquaintance as a passenger.

7. The method of claim 1, further comprising:
   integrating computer-readable program code into a computer system comprising a processor, a computer readable memory in circuit communication with the processor, and a computer readable storage medium in circuit communication with the processor; and
   wherein the processor executes program code instructions stored on the computer-readable storage medium via the computer readable memory and thereby performs the steps of determining the well-being objective of the traveler, determining the amount of the indicated amount of the human-powered transport option that the traveler is currently able to perform in reaching the destination, and generating the recommended route to the destination from the current location that meets the well-being objective.

8. The method of claim 1, wherein the traveler's current location is a current floor level in a multi-story building, the target destination is a destination floor level in the multi-story that is different from the current floor level, the amounts of the human-powered transport option that the traveler is currently able to perform are flight distance amounts of stairways of the multi-story building, and the motorized transport option is an elevator that conveys passengers between the current floor level and the different floor level; and
wherein the step of generating the recommended route comprises including a motorized route portion that comprises riding the elevator from the current floor level to an interim floor level of the multi-story building, wherein the interim floor level is different from the destination floor level, and including a human-powered route portion that comprises a specified flight distance amount of the stairways that extends from the interim floor level to the destination floor level and does not exceed the amounts of the human-powered transport option that the traveler is currently able to perform.

9. The method of claim 8, wherein the step of generating the recommended route further comprises:
excluding a human-powered route portion that comprises an alternative flight distance amount of the stairways that extends from another, different interim floor level to the destination floor level from the route as a function of the alternative flight distance amount exceeding the amount of the human-powered transport option that the traveler is currently able to perform.

10. A system, comprising:
a processor;
a computer readable memory in circuit communication with the processor; and
a computer readable storage medium in circuit communication with the processor;
wherein the processor executes program instructions stored on the computer-readable storage medium via the computer readable memory and thereby:
determines a well-being objective of a traveler that is selected from the group consisting of meeting an exercise goal, minimizing exposure to an environmental stressor, and limiting a physical demand placed on the traveler by exertion required to perform a human-powered transport option to a maximum amount, and wherein the environmental stressor is selected from the group consisting of a poor weather condition, a poor smog level condition and a poor ozone level condition;
determines an amount of the human-powered transport option for the traveler to perform to meet requirements of the well-being objective; and
generates a recommended route to a destination from a current location of the traveler that meets the well-being objective by selecting between route segment portions of usage of the human-powered option and of a motorized transport option, by including selections from the group consisting of:
including a first segment of usage of the human-powered transport option in response to said included first segment requiring an amount of effort that meets the well-being objective and does not exceed an amount of the human-powered transport option that the traveler is currently able to perform; and
excluding a second segment of usage of the human-powered transport option in response to said excluded second segment requiring an amount of effort that does not meet the well-being objective or that exceeds the amount of the human-powered transport option that the traveler is currently able to perform.

11. The system of claim 10, wherein the well-being objective comprises a goal to maximize a well-being of the traveler by including a use of the human-powered transport option for a portion of the generated route in an amount that meets the exercise goal of the traveler.

12. The system of claim 10, wherein the processor executes the program instructions stored on the computer-readable storage medium via the computer readable memory and thereby determines the amount of the human-powered transport option that the traveler is currently able to perform by:
comparing real-time health monitor data indicative of the current status of the traveler to expected health monitor data values for the traveler; and
in response to determining that the real-time health monitor data of the traveler is lower than the expected health monitor data values, reducing an amount of the human-powered transport option that the traveler is currently able to perform.

13. The system of claim 10, wherein the processor executes the program instructions stored on the computer-readable storage medium via the computer readable memory and thereby:
analyzes social network data of the traveler to identify a friend of the traveler that is desirable for selection as a fellow motorized transport option passenger, or to identify another acquaintance of the traveler that is undesirable for selection as a fellow motorized transport option passenger; and
generating the recommended route by including a step selected from the group consisting of selecting a route segment of usage of the motorized transport option that includes the friend as a passenger, and omitting a route segment of usage of the motorized transport option that includes the another acquaintance as a passenger.

14. The system of claim 10, wherein the traveler's current location is a current floor level in a multi-story building, the target destination is a destination floor level in the multi-story that is different from the current floor level, the amounts of the human-powered transport option that the traveler is currently able to perform are flight distance amounts of stairways of the multi-story building, and the motorized transport option is an elevator that conveys passengers between the current floor level and the different floor level; and
wherein the processor executes the program instructions stored on the computer-readable storage medium via the computer readable memory and thereby generates the recommended route to comprise a motorized route portion of riding the elevator from the current floor level to an interim floor level of the multi-story building, wherein the interim floor level is different from the destination floor level; and a human-powered route portion that comprises a specified flight distance amount of the stairways that extends from the interim floor level to the destination floor level and does not exceed the amounts of the human-powered transport option that the traveler is currently able to perform.

15. The system of claim 14, wherein the processor executes the program instructions stored on the computer-readable storage medium via the computer readable memory and thereby further generates the recommended route by excluding a human-powered route portion that comprises an alternative flight distance amount of the stairways that extends from another, different interim floor level to the destination floor level from the route as a function of the alternative flight distance amount exceeding the amount of the human-powered transport option that the traveler is currently able to perform.

16. A computer program product for automatically selecting between human-powered and motorized transport options to produce a route to a destination to meet a traveler well-being objective, the computer program product comprising:
  a computer readable storage medium having computer readable program code embodied therewith, wherein the computer readable storage medium is not a transitory signal per se, the computer readable program code comprising instructions for execution by a processor that cause the processor to:
  determine a well-being objective of a traveler that is selected from the group consisting of meeting an exercise goal, minimizing exposure to an environmental stressor, and limiting a physical demand placed on the traveler by exertion required to perform a human-powered transport option to a maximum amount, and wherein the environmental stressor is selected from the group consisting of a poor weather condition, a poor smog level condition and a poor ozone level condition;
  determine an amount of the human-powered transport option for the traveler to perform to meet requirements of the well-being objective; and
  generate a recommended route to a destination from a current location of the traveler that meets the well-being objective by selecting between route segment portions of usage of the human-powered option and of a motorized transport option, by including selections from the group consisting of:
  including a first segment of usage of the human-powered transport option in response to said included first segment requiring an amount of effort that meets the well-being objective and does not exceed an amount of the human-powered transport option that the traveler is currently able to perform; and
  excluding a second segment of usage of the human-powered transport option in response to said excluded second segment requiring an amount of effort that does not meet the well-being objective or that exceeds the amount of the human-powered transport option that the traveler is currently able to perform.

17. The computer program product of claim 16, wherein the well-being objective comprises a goal to maximize a well-being of the traveler by including a use of a human-powered transport option for a portion of the generated route in an amount that meets an exercise goal of the traveler; and
  wherein the computer readable program code instructions for execution by the processor further cause the processor to:
  analyze social network data of the traveler to identify a friend of the traveler that is desirable for selection as a fellow motorized transport option passenger, or to identify another acquaintance of the traveler that is undesirable for selection as a fellow motorized transport option passenger; and
  generate the recommended route to meet the well-being objective by including a step selected from the group consisting of selecting a route segment of usage of the motorized transport option that includes the friend as a passenger, and omitting a route segment of usage of the motorized transport option that includes the another acquaintance as a passenger.

18. The computer program product of claim 16, wherein the traveler's current location is a current floor level in a multi-story building, the target destination is a destination floor level in the multi-story that is different from the current floor level, the amounts of the human-powered transport option that the traveler is currently able to perform are flight distance amounts of stairways of the multi-story building, and the motorized transport option is an elevator that conveys passengers between the current floor level and the different floor level; and
  wherein the computer readable program code instructions for execution by the processor further cause the processor to generate the recommended route to comprise:
  a motorized route portion that comprises riding the elevator from the current floor level to an interim floor level of the multi-story building, wherein the interim floor level is different from the destination floor level; and
  a human-powered route portion that comprises a specified flight distance amount of the stairways that extends from the interim floor level to the destination floor level and does not exceed the amounts of the human-powered transport option that the traveler is currently willing, able or recommended to perform.

19. The computer program product of claim 18, wherein the computer readable program code instructions for execution by the processor further cause the processor to generate the recommended route by excluding a human-powered route portion that comprises an alternative flight distance amount of the stairways that extends from another, different interim floor level to the destination floor level from the route as a function of the alternative flight distance amount exceeding the amount of the human-powered transport option that the traveler is currently able to perform.

20. The computer program product of claim 19, wherein the amount of the human-powered transport option that the traveler is currently able to perform is selected from the group consisting of:
  a distance travelled;
  a step count;
  a number of flights of stairs;
  an amount of elevation gained or lost;
  an elapsed time of travel;
  a number or rate of calories burned;
  a specified value or range of values of heart rate of the traveler; and
  a power output value.

* * * * *